(12) United States Patent
Jensen (10) Patent No.: US 7,211,813 B2
(45) Date of Patent: May 1, 2007

(54) HIGH-INTENSITY UV-C GUN AND METHODS OF USE

(76) Inventor: Erick C. Jensen, 141 W. Louther St., Carlisle, PA (US) 17013

( * ) Notice: Subject to any disclaimer, the term of this patent is extended or adjusted under 35 U.S.C. 154(b) by 10 days.

(21) Appl. No.: 11/179,314

(22) Filed: Jul. 12, 2005

(65) Prior Publication Data

US 2006/0017025 A1   Jan. 26, 2006

Related U.S. Application Data (60) Provisional application No. 60/590,169, filed on Jul. 22, 2004.

(51) Int. Cl.
 *G01J 3/10* (2006.01)
 *G01J 1/00* (2006.01)
(52) U.S. Cl. .............. 250/504 H; 250/504 R; 362/293; 362/202; 362/109
(58) Field of Classification Search ............. 250/504 H
 See application file for complete search history.

(56) References Cited

U.S. PATENT DOCUMENTS

| | | | |
|---|---|---|---|
| 2,215,635 A | | 9/1940 | Collins |
| 4,149,086 A | * | 4/1979 | Nath ........................ 250/504 R |
| 4,786,812 A | * | 11/1988 | Humphreys ............ 250/455.11 |
| 4,877,964 A | | 10/1989 | Tanaka et al. |
| 4,952,369 A | | 8/1990 | Belilos |
| 5,216,322 A | * | 6/1993 | Fuchs ......................... 313/484 |
| 5,634,711 A | * | 6/1997 | Kennedy et al. ............. 362/119 |
| 5,788,364 A | * | 8/1998 | Cooper et al. .............. 362/293 |
| 5,816,692 A | * | 10/1998 | Cooper et al. .............. 362/293 |
| 5,894,130 A | | 4/1999 | Bach |
| 5,920,075 A | | 7/1999 | Whitehead |
| 5,968,455 A | | 10/1999 | Brickley |
| 5,997,154 A | * | 12/1999 | Cooper et al. .............. 362/293 |

(Continued)

OTHER PUBLICATIONS

PHYSLINK.COM, "What is the wavelength of UVa, UVb, and UVc light measured in nanometers, and frequency (in Hz)?" http://www.physl;ink.com/Education/AskExperts/ae300.cfm.*

(Continued)

*Primary Examiner*—Nikita Wells
*Assistant Examiner*—Bernard Souw
(74) *Attorney, Agent, or Firm*—McNees Wallace & Nurick LLC (57) ABSTRACT

A portable high-intensity ultraviolet (UV-C) light gun is provided, the gun comprised of a high-intensity UV-C emitting light bulb mounted into a gun assembly. The gun assembly includes means for gathering and directing the high-intensity light emitted from the bulb and focusing the light into a beam that can be directed to a target. The gun assembly includes a light box that includes a bulb mount having electrical terminals for electrically connecting a UV bulb to a power source, and further includes a mirror for gathering and reflecting the emitted light towards an opening provided in the light box. One end of an elongated cylindrical hollow light tube is connected to the opening for channeling and focusing the emitted and reflected light from the light box toward the opposite open end of the tube. The tube can include a nozzle for further focusing and directing of the emitted light. Methods of using the gun to eradicate pathogens and other biological organisms are also provided.

20 Claims, 5 Drawing Sheets

U.S. PATENT DOCUMENTS

| | | |
|---|---|---|
| 6,090,346 A | 7/2000 | Rose et al. |
| 6,264,888 B1 | 7/2001 | Palestro et al. |
| 6,493,986 B1 * | 12/2002 | Nelson et al. ............... 43/113 |
| 6,497,840 B1 | 12/2002 | Palestro et al. |
| 6,637,913 B2 * | 10/2003 | Sei et al. ............... 362/373 |
| 6,644,835 B2 * | 11/2003 | Sei et al. ............... 362/373 |
| 6,656,424 B1 | 12/2003 | Deal |
| 6,692,694 B1 * | 2/2004 | Curry et al. ............... 422/28 |
| 2002/0032980 A1 * | 3/2002 | Nelson ............... 43/113 |
| 2002/0098109 A1 * | 7/2002 | Nelson et al. ............... 422/5 |
| 2003/0039577 A1 * | 2/2003 | Nelson et al. ............... 422/4 |
| 2003/0089023 A1 * | 5/2003 | Nelson et al. ............... 43/113 |
| 2004/0219057 A1 * | 11/2004 | Golden ............... 422/24 |
| 2005/0175498 A1 * | 8/2005 | Nelson et al. ............... 422/4 |
| 2005/0254237 A1 * | 11/2005 | Nath et al. ............... 362/190 |
| 2005/0276072 A1 * | 12/2005 | Hayashi et al. ............... 362/609 |
| 2006/0017025 A1 * | 1/2006 | Jensen ............... 250/504 R |
| 2006/0040231 A1 * | 2/2006 | Quan et al. ............... 433/29 |
| 2006/0157426 A1 * | 7/2006 | Petrie ............... 210/748 |
| 2006/0259101 A1 * | 11/2006 | Perez ............... 607/88 |

OTHER PUBLICATIONS

Biocompare, "Spectrometry Light Sources", http://www.biocompare.com/matrix/15380/Spectrometry-Light-Sources.html.*

* cited by examiner

HIGH-INTENSITY UV-C GUN AND METHODS OF USE

BACKGROUND OF THE INVENTION

The present invention relates generally to a portable high-intensity ultraviolet light gun that produces a narrow focused beam of ultraviolet radiation, and also to methods of using the light gun. With respect to methods, the gun can be used in performing remediation of environmental surface mold, mildew, and other undesirable biological material in a non-aqueous environment. Additionally, the light gun could also potentially be used as a weapon, such as in self-defense use or in military combat, to project a stream of harmful ultraviolet light onto an attacker to cause temporary or permanent physical injury such as eye and skin damage.

The use of ultraviolet light ("UV"), and particularly UV-C, for eradicating pathogens and microbiological organisms, is known in the prior art. Indeed, several devices for emitting UV for such purposes are known and described in issued patents, including U.S. Pat. No. 6,656,424 (the '424 Patent); U.S. Pat. No. 5,920,075 (the '075 patent); U.S. Pat. No. 4,952,369 (the '369 Patent); and U.S. Pat. No. 2,215,635 (the '635 patent).

The '424 patent is directed to a mobile ultraviolet area sterilizer having UV-C generators such as a bank of mercury bulbs, to generate intense levels of UV-C for sterilization of surfaces such as the surfaces of a hospital operation room. The '424 patent discloses a portable apparatus that can be used to deliver bactericidal doses of UV-C broadly outward from the provided cylindrical bank of bulbs when the device is placed in an unmanned room and operated. The device disclosed in the '424 patent, while suited for large areas, cannot be effectively utilized in small areas such as crawlspaces, and cannot treat cracks and crevices. Additionally, while the device is somewhat portable within smooth-floored buildings, it is very large and cumbersome, and must be moved on wheels. Additionally, the circumferential arrangement of exposed bulbs makes the device fragile and likely to incur damage if dropped or jarred during transit or use. Lastly, the device does not produce a focused beam of UV that can be directed at a particular target while minimizing UV exposure to surrounding areas.

The '075 patent is directed to a handheld sterilization device that emits ultraviolet radiation in a range sufficient to eradicate germs, bacteria, viruses, and other pathogens and microorganisms. The device includes a housing containing a UV light source, a power source, and an electronic safety mechanism. The device disclosed in the '075 patent includes a UV bulb sufficient to provide approximately 2000–6000 microwatts/cm$^2$. The device is coupled to a power supply such as a power cord of sufficient length to allow an operator to reach all areas of a room to be treated, and an alternate power supply provided as a battery. A locking set of doors act as a hood to cover the bulb when the device is locked or powered off. However, there is no discussion or suggestion in the '075 patent of producing a narrowly focused beam of UV-C light, a cooling fan for cooling the bulb, or attachment of a HEPA vacuum.

The '369 patent is directed to a portable handheld sterilization device that emits ultraviolet radiation in a range sufficient to eradicate germs and viruses. The device includes a housing containing a UV light source, a power source, and an on-off gravity switch that is activated only when the light source is facing downwards. The device is coupled to a power supply such as a battery, and can have a converter to convert battery power to a higher voltage. There is no discussion or suggestion in the '369 patent of a light tube or other means for producing a focused beam of light, a cooling fan for cooling the bulb, or attachment of a HEPA vacuum.

The '635 patent is directed to an apparatus that emits an intense beam of ultraviolet radiation in a range sufficient to eradicate germs and viruses. The beam is produced in conjunction with a beam of visible light for illumination of a patient in an operating room. The intensity and focus of the UV light can be adjusted by an operator so as to maintain a level sufficient to eradicate pathogens, but not to cause unwanted effects to the patient. The '635 patent discusses adjustment of the amount of current supplied to the bulb using a rheostat. There is no discussion or suggestion in the '635 patent of a handheld UV-C device. Nor is there any discussion or suggestion of providing a light tube for producing a focused beam of light, a cooling fan for cooling the bulb, or the attachment of a HEPA vacuum.

What is needed is a portable, durable, handheld UV light gun that provides a powerful and focused beam of UV-C radiation that be precisely targeted to effectively eradicate biological contaminants with minimal exposure to surrounding areas or the operator.

What is further needed is a UV light gun having a cooling fan for maintaining the UV bulb at an operating temperature that will preserve the life of the bulb, minimize heat exposure to the surrounding housing and components, and allow an operator to comfortably operate the device in close quarters such as crawlspaces.

Additionally, what is needed is a handheld portable UV gun including features to allow attachment and concurrent use of a HEPA vacuum to remove treated contaminants from areas treated using the UV gun.

Further, what is needed is a UV gun having means for automatically disabling the gun when unintended exposure to a human would otherwise result.

SUMMARY OF THE INVENTION

One embodiment of the present invention is directed to a portable high-intensity ultraviolet (UV-C) light gun comprised of a high-intensity UV-C emitting light bulb mounted into a gun assembly, the gun assembly including means for gathering and directing the high-intensity light emitted from the bulb and focusing the light into a beam that can be directed to a target. The gun assembly includes a light box that includes a bulb mount having electrical terminals for electrically connecting a UV bulb to a power source. The light box further includes a mirror for gathering and reflecting the emitted light towards an opening provided in the light box. One end of an elongated cylindrical hollow light tube is connected to the opening for channeling and focusing the emitted and reflected light from the light box toward the opposite open end of the tube. The tube can further include a nozzle for further focusing and directing of the emitted light. The tube is preferably a lightweight metallic or composite material, and the inner surface of the tube includes a polished inner surface or sleeve for reflecting light passing through the tube. The light exiting the open end or nozzle of the light tube is produced as a relatively narrow beam pattern, similar in pattern to a flashlight, and can be easily directed at a selected surface.

In one embodiment, the methods of the present invention include providing a surface having biological contaminants thereon, operating a portable ultraviolet light gun having an elongated tube for emitting ultraviolet light in a focused and directed beam, and emitting and directing the light to at least one target on the surface for a time sufficient to eradicate a biological contaminant on the surface.

In another embodiment, the methods of the present invention include providing a biological organism, operating a portable ultraviolet light gun having an elongated tube for emitting ultraviolet light in a focused and directed beam, and emitting and directing the light to strike the organism in a manner so as to cause physical injury to the organism sufficient to render the organism substantially incapacitated.

BRIEF DESCRIPTION OF THE DRAWINGS

Wherever possible, the same reference numbers will be used throughout the drawings to refer to the same or like parts.

DETAILED DESCRIPTION OF THE INVENTION

The subject matter of the invention under consideration is directed to a high-intensity ultraviolet light gun 100, and methods of using the gun. The gun is a significant improvement over existing UV light sources for environmental remediation of microorganisms because it is easy to carry and use, is entirely portable, and works faster. Additionally, because the gun generates a focused beam of UV light, it can be used by technicians without having to leave the room, and can also be safely operated with a minimum of UV protective gear.

Figure 1:
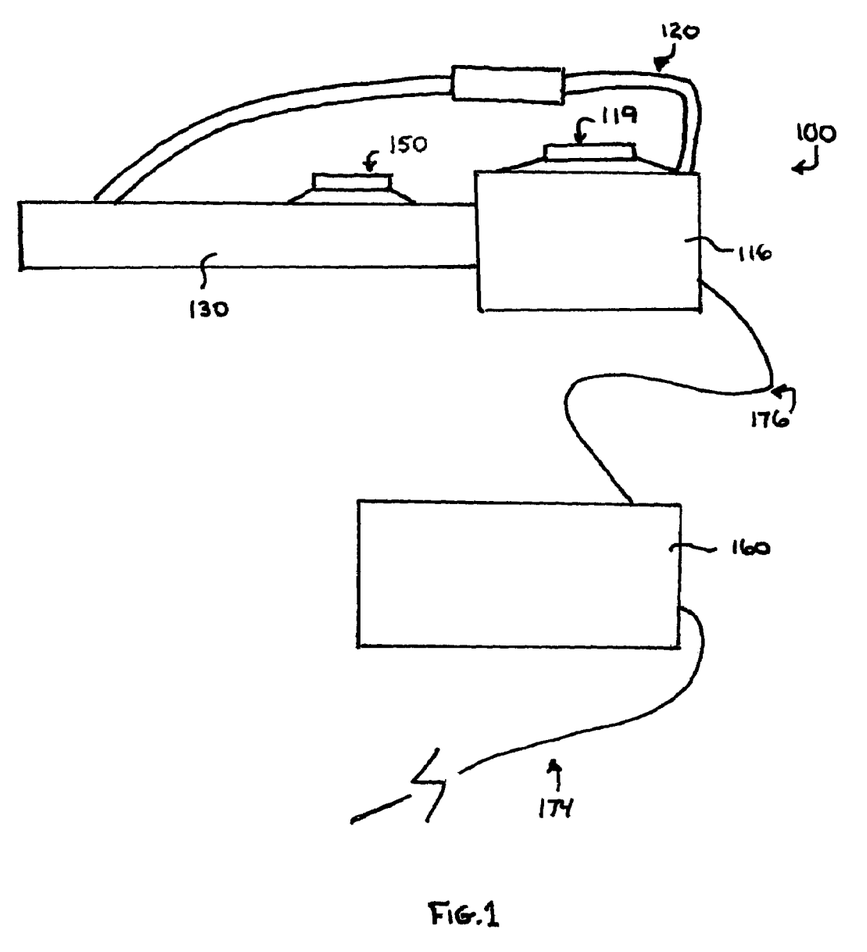
FIG. 1 illustrates a side perspective view of one embodiment of the light gun and power supply of the present invention in accordance with the present invention.
Figure 2:
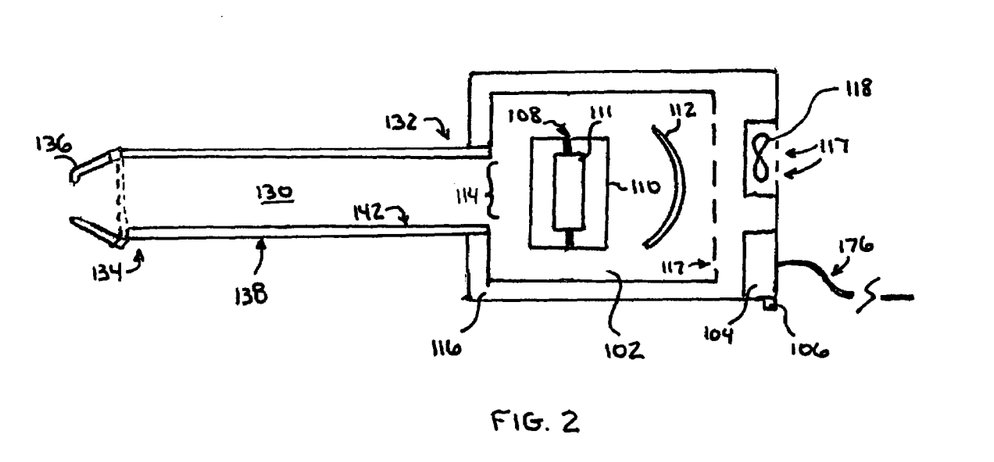
FIG. 2 illustrates a top cross-sectional view of the embodiment of the light gun of FIG. 1 in accordance with the present invention.
Figure 3:
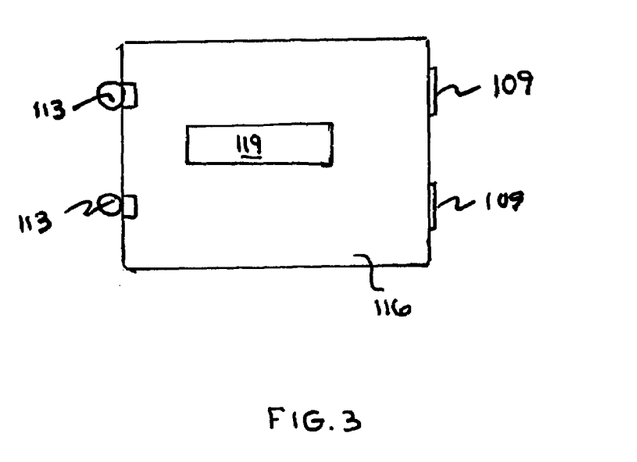
FIG. 3 illustrates a top perspective view of the light gun of FIG. 1 in accordance with the present invention.
Figure 4:
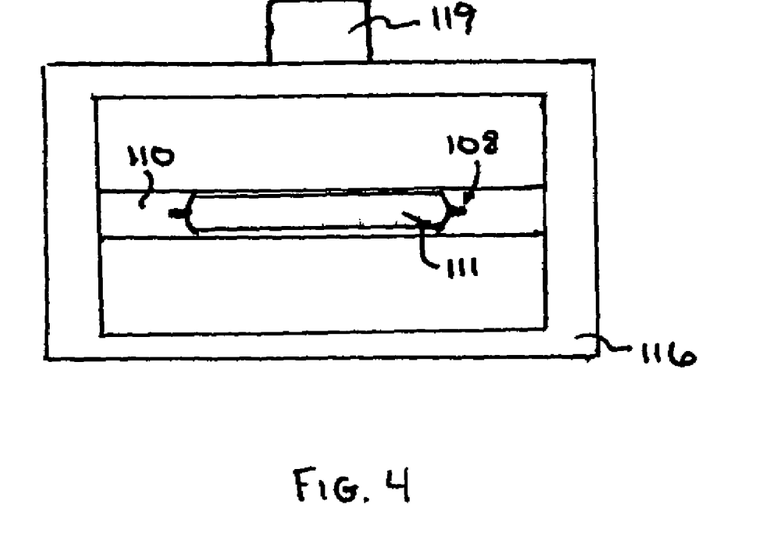
FIG. 4 illustrates a front cross-sectional view of the light box of the light gun of FIG. 1 in accordance with the present invention.
Figure 5:
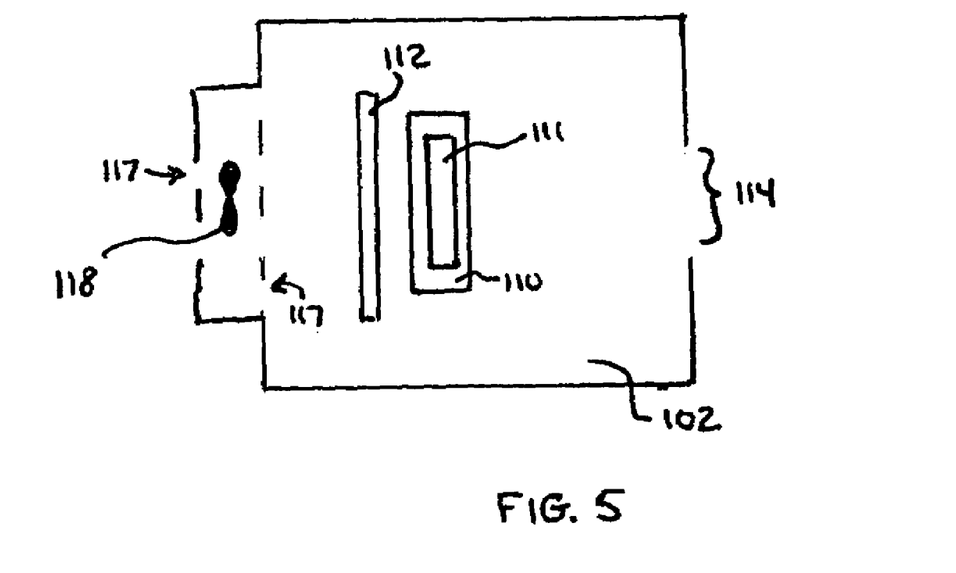
FIG. 5 illustrates a top partial cross-sectional view of the light box of the light gun of FIG. 1 in accordance with the present invention.

As shown in FIG. 1–3, the invention is comprised of an assembly of a light gun 100 having a housing portion 116 containing a light box 102, the light box 102 communicably connected to a barrel 130 for emitting UV from the light box 102 through the barrel 130. The light gun 100 is electrically connected to a power supply 160 that is connected to a power source by a first power cord 174 for providing high-voltage electricity through a second power cord 176 to a high-intensity, UV-C emitting light bulb 111 mounted within the light box 102. The light gun 100 preferably also includes one or more handles 119, 150 for use by an operator in transporting and operating the light gun 100. Additionally, the housing 102 preferably includes means for opening the housing 102 to provide access to the internal components such as the bulb 111. As shown in FIG. 3, the access means preferably include one or more hinges 109 to provide clamshell-type opening of the top of the housing 102, and preferably further include clasps or locks 113 provided on a non-hinged wall adjacent the hinged top portion of the housing 102.

As shown in FIGS. 2–5, the gun 100 includes features for generating and directing a high-intensity stream of UV, preferably UV-C, to a target to expose the target to high-intensity UV. The gun 100 includes a light box 102 mounted within an outer housing 116. The light box 102 includes a bulb mount 110 for releasably but securely retaining a UV bulb 111. The light mount can include spring retainer clips, slots, or other retaining means known to those skilled in the art of lighting mountings and fixtures. The mount 110 positions the bulb so that the bulb contacts one or more provided electrical bulb terminals 108 to complete a high-voltage electrical circuit. The electrical bulb terminals 108 are in turn electrically connected to an electrical panel 104. The electrical panel 104 receives electricity from the power supply 160, which electricity may be provided through a power cord 176 linked to an external power source, and/or by batteries. The electrical panel 104 also provides power to at least one fan 118 provided within the housing 116 of the light gun 100 for cooling the bulb 111 and other gun components. Electrical supply from the panel to the bulb 111, fan 118 and any other electrical component is controlled by one or more switches 106 that can be operated by the user to selectively turn the components on or off. Preferably, the panel 104 and/or the switches 106 include features such as timers or microprocessor controls to ensure that electrical supply to the fan 118 is maintained as necessary to preserve the life of the bulb 111 and surrounding components, such as by operating the fan 118 for a time after power to the bulb 111 is turned off. Moreover, in a preferred embodiment, the gun 100 includes a timer in conjunction with a motion sensing switch to allow unmanned use of the gun 100 for a predetermined time, while simultaneously monitoring the environment of the unmanned operating gun 100 for any unauthorized persons. The motion sensing switch can include a motion sensor, and preferably can also be linked to commercially available external motion sensors that can be placed at strategic locations such as doors, windows, stairs, and other access points. Upon sensing motion at any such sensor, the motion sensing switch will shut off power to the bulb 111, but may continue to allow power to operate the cooling fan 118 and other non-hazardous elements of the gun.

Figure 6:
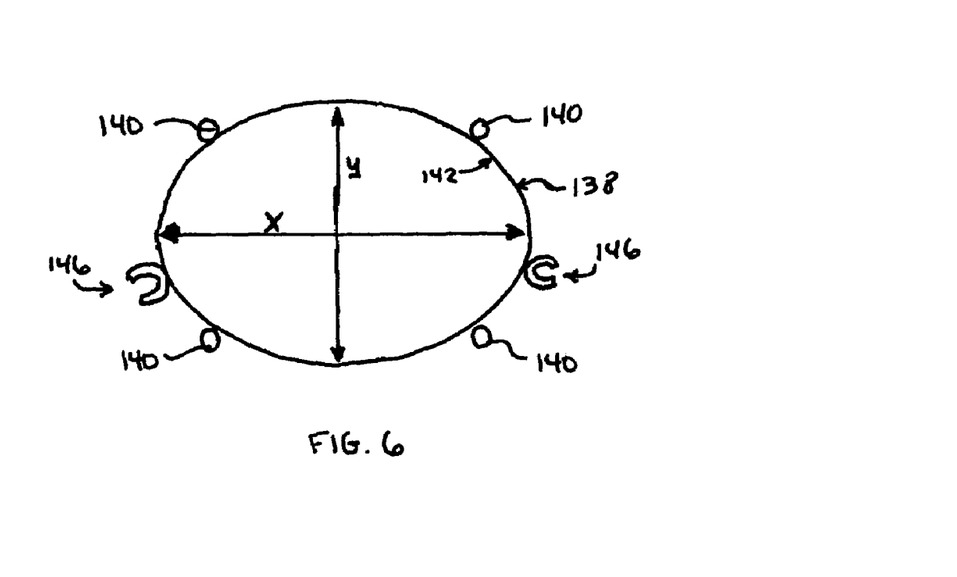
FIG. 6 illustrates a front cross-sectional view of the barrel of the light gun of FIG. 1 in accordance with the present invention.
Figure 7:
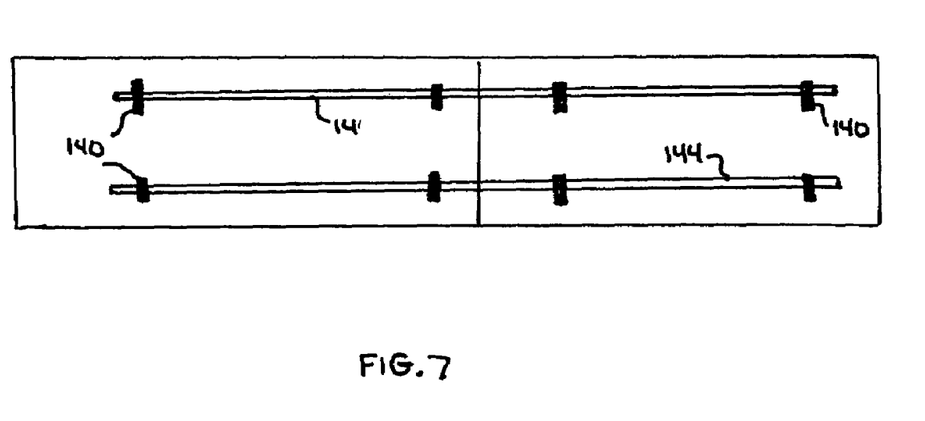
FIG. 7 illustrates a side perspective view of the barrel of the light gun of FIG. 1 in accordance with the present invention.

The light box 102 includes a mirror 112 for gathering and reflecting the emitted UV towards a light opening 114 provided in the light box 102. A first end 132 of a barrel 130 is connected to the light opening 114 for channeling and focusing the emitted and reflected UV towards an opposite open end 134 of the barrel 130. As shown in FIGS. 6–7, in one embodiment, the barrel 130 is provided as a lightweight elongated and generally cylindrical hollow tube. As used herein, "substantially cylindrical" means the barrel 130 has a circular or oval or ovaloid cross-sectional geometry in at least one location along its longitudinal axis, which geometry is defined by a major axis X and a minor axis Y, as shown in FIG. 6. The barrel 130 is preferably a lightweight thin steel outer tube 138. Preferably, the barrel 130 has a reflective inner surface 142, such as a polished metallic surface. Alternatively, the reflective surface can be provided using an inner sleeve, such as a polished aluminum inner sleeve, inserted into the barrel 130.

UV light emitted by the bulb 111 and reflected by the mirror 112 travels into the opening provided at the first end 132 of the barrel 130 and out of the second end 134 of the barrel. Preferably, a nozzle 136 is provided adjacent the second end 134 so that the UV light can be selectively adjusted from a wide beam to a narrow beam pattern. The nozzle 136 may be comprised of fixed diameter modules that screw or slide onto the second end 134, and/or may include iris-like or telescoping adjustments such as those provided in adjustable beam flashlights.

The barrel 130 can be provided as a single continuous tube, or may be provided as a series of two or more modular pieces that can be removably connected. The benefit of the modular barrel is that it provides greater flexibility. For example, an operator can elect to use a single piece short barrel 130 in tight quarters such as crawlspaces, or add barrel modules to create a longer barrel with greater reach for treatment of remote surfaces such as cracks, crevices, ceilings, and the like. In the embodiment shown in FIG. 7, the outer surface 138 of the barrel 130 includes means 140 for interconnecting barrel modules. Preferably, the means includes loops or cylinders 140 on the outer surface 138 for receiving cylindrical rods 144, thus allowing interconnection of barrel modules. Other barrel connection means include tabs and slots, threads, and friction fittings, as well as other connection means known to those skilled in the art.

Additionally, the outer surface 138 can include means, such as hose clamps 146 or other holding means. As shown in FIG. 6, the clamps 146 can be provided for attaching remediation apparatus such as a HEPA vacuum hose to the barrel 130 to simultaneous treatment and removal by suction of the contaminants. Additionally or alternatively, clamps 146 may be provided on the barrel surface 138 and/or the housing 102 to hold power cords, hoses, unused nozzles 136 and extra barrel sections 130, as well as other ancillary remediation equipment.

Using selection of the bulb 111, electrical power input, barrel 130 types and length, and nozzle 136 configuration, a UV-C beam can be provided that is powerful enough to eradicate surface mold even at a distance of ten feet from the surface. For example, in one embodiment incorporating a 4 inch long 1000 watt UV-C bulb 111 mounted horizontally in a cube-shaped light box 102 having internal sides of approximately 8.5 inches, and having a parabolic polished aluminum mirror 112 therein, and further having a nozzleless substantially cylindrical polished aluminum barrel 130 approximately 4 inches in diameter and approximately 24 inches in length, the projected beam covered a wall area approximately 6 feet wide by 6 feet tall at distance of ten feet from the wall. The emitted and focused high-intensity UV-C light was believed to be effective at remediating environmental mold and other undesirable microbiological organisms on the surface within seconds of focusing the beam of emitted UV on the surface. In another embodiment, a 750 watt UV-C bulb is used. However, a broad wattage selection of UV-C bulbs can be effectively used in combination with various embodiments of the disclosed light gun to accomplish the desired results for various surfaces and environments depending upon the desired time of exposure and desired coverage area. For example, the bulb can be a low pressure-amalgam or medium pressure-amalgam UV-C bulb, and can be used with our without a quartz sleeve. Such germicidal UV-C bulbs can be supplied by commercial fabricators and distributors. Without limiting the scope of the bulbs that can be used, the below tables are illustrative of bulbs offered by The UV Doctor (www.uvdoctor.com) that can be used in accordance with the invention:

TABLE 1

EXEMPLARY LOW PRESSURE UV LAMPS

| UVDR PN | LAMP REPLACEMENTS FOR | ENDS | WATTS | APPLICATION |
| --- | --- | --- | --- | --- |
| UVDRX-1172 | Trojan 3000 | SE | 65 W | DISINFECTION |
| UVDRX-1174 | AQUAFINE 17998 | SE | 65 W | DISINFECTION |
| UVDRX-1176 | FISHER PORTER | SE | 65 W | DISINFECTION |
| UVDRX-1177 | IDI/ULTRA TECH | SE | 65 W | DISINFECTION |
| UVDRX-1179 | G64/254 nm | DE/SP | 65 W | DISINFECTION |

TABLE 2

EXEMPLARY MEDIUM PRESSURE UV LAMPS

| LAMPS | UVDR PN | REPLACES | DESC | WATTS | APPLICATION |
| --- | --- | --- | --- | --- | --- |
| Validated | UVDRX 1401 | B2000 | DE | 2000 W | Disinfection |
| Validated | UVDRX 1402 | B4000 | DE | 4000 W | Disinfection |
| Validated | UVDRX 1404 | B2035 | DE | 2000 W | Disinfection |
| Validated | UVDRX 1407 | B2020 | DE | 2000 W | Disinfection |
| Validated | UVDRX 3535 | B3535 | DE | 3500 W | Disinfection |
| Validated | UVDRX 12515 | UV250 XP | SE/DE | 1500 W | Disinfection |
| Validated | UVDRX 12520 | UV500 XP | SE/DE | 2000 W | Disinfection |
| Validated | UVDRX 12522 | UV2000 | SE/DE | 2000 W | Disinfection |
| Validated | UVDRX 12535 | UV2500 | SE/DE | 3500 W | Disinfection |
| Validated | UVDRX 12550 | UV4000 | SE/DE | 5000 W | Disinfection |

TABLE 3

EXEMPLARY CELL LAMPS (ONE PIECE LAMP AND QUARTZ)

| LAMP | UVDR PN | REPLACES AQUAFINE TYPE | DESC | LENGTH | APPLICATION |
| --- | --- | --- | --- | --- | --- |
| Validated Cell | UVDRX 1352 | 17491/17751 | 254 nm | 30" STD | Disinfection/Ozone |
| Validated Cell | UVDRX 1380 | 17998/18056 | 254 nm | 60" STD | Disinfection/Ozone |

TABLE 3-continued

EXEMPLARY CELL LAMPS (ONE PIECE LAMP AND QUARTZ)

| LAMP | UVDR PN | REPLACES AQUAFINE TYPE | DESC | LENGTH | APPLICATION |
|---|---|---|---|---|---|
| Validated Cell | UVDRX 1353 | 18198/17751 | 254 nm | 30" HE | Disinfection/Ozone |
| Validated Cell | UVDRX 1358 | 18063/17751 | 185 nm | 30" STD | TOC |
| Validated Cell | UVDRX 1384 | 17498/18056 | 185 nm | 60" STD | TOC |
| Validated Cell | UVDRX 1359 | 18197/17751 | 185 nm | 30" HE | TOC |
| Validated Cell | UVDRX 1385 | 17820/18056 | 185 nm | 60 HE | TOC |

The light box 102 further includes a fan 118 for pulling air through air vent openings 117 provided in the light box 102 and for pulling cooling air across the bulb 111. Preferably, the fan is of a lightweight durable material such as aluminum, other metals, or plastic. Preferably, cooling air is pulled through the barrel 130, across the bulb 111, through the vents 117, through the housing 116, and out of the housing vent openings 117. Filters and screens can be provided at any of all of the vents 117 to capture contaminants.

Figure 8:
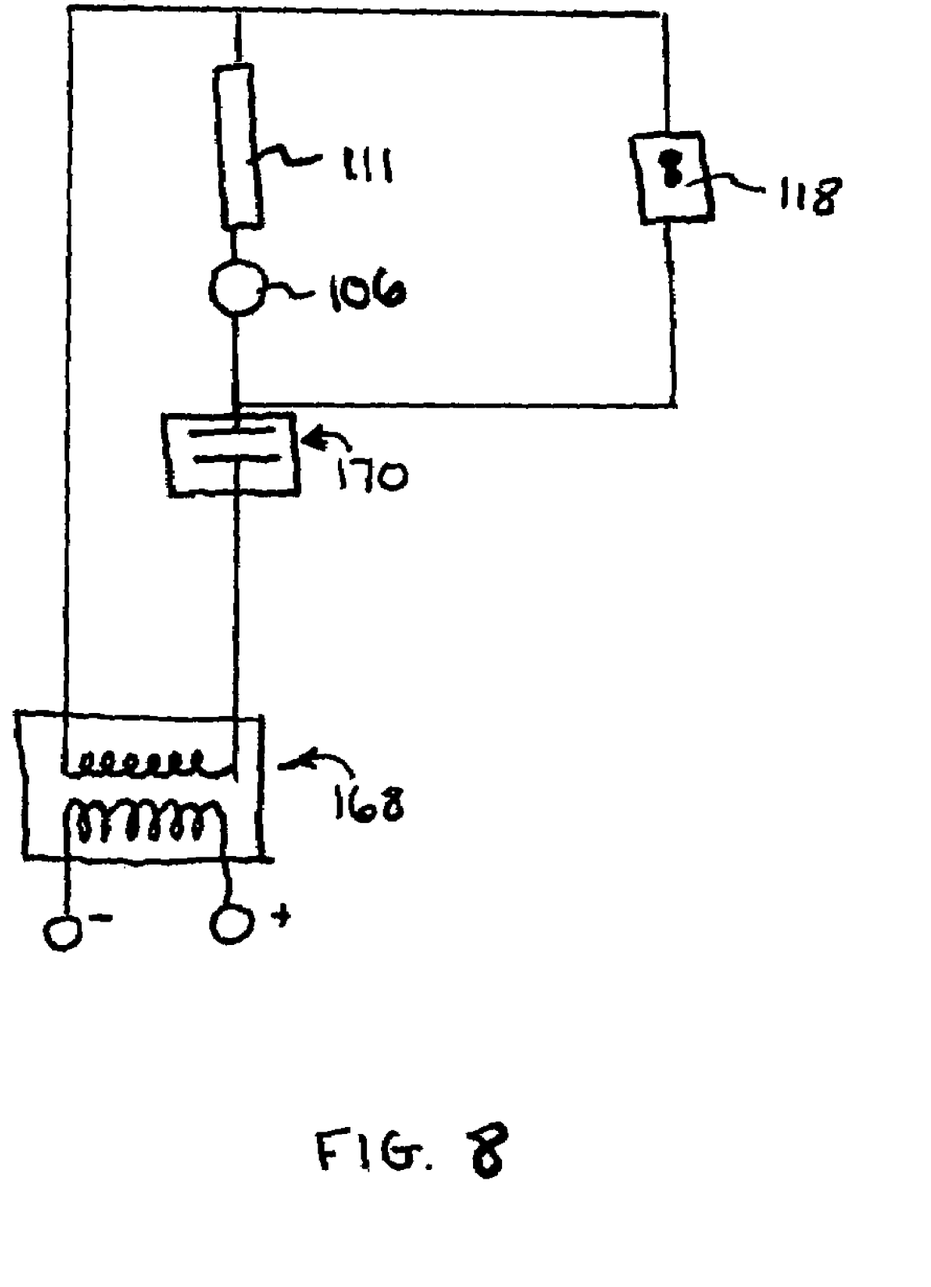
FIG. 8 illustrates an electrical wiring diagram for the light gun in accordance with the present invention.

As shown in FIG. 1 and FIG. 8, the gun 100 is electrically connected to a power supply 160 for providing electrical power to the bulb 111 and other components. The power supply 160 preferably includes at least one capacitor 170 and at least one transformer 168 as necessary to power the bulb 111 from a standard 110-volt power source, such as a residential outlet of a home having contaminated surfaces to be remediated. An exemplary electrical circuit diagram for the power supply 160 is provided as FIG. 8. As previously described, the power supply 160 is linked to the gun 100 by a long power cord 176 so as to allow use of the gun 100 in locations remote from the power supply 160. Preferably, where a power cord 176 is provided, the power supply 160 includes a housing 116 having recessed electrical prongs for receiving the power cord 176 such that there is no portion of any electrical prong exposed, thereby avoiding the risk of unintended contact by a user and associated undesirable electrical shock.

In other embodiments, the power supply 160 components can be located within the housing 116 of the gun 100. In one embodiment, the power supply 160 can include rechargeable batteries as the electrical power source, such as in a 250 watt, 750 watt, or 1000 watt embodiment. In still another embodiment, the power supply 160 components such as transformers and capacitors, and optionally batteries, are included in the housing 116 in proximity to the light box 102, and are preferably protected by metal wrapping and shielding to prevent degradation of the components and associated wiring by heat or UV exposure. In this embodiment, the gun 100 can either be battery powered, or can simply be plugged into a standard 110-volt outlet.

The gun assembly further includes one or more handles 119, 150 for carrying the gun and for directing light emitted from the barrel 130 towards a selected target area. As shown in FIG. 1, the handles 119, 150 can be located on the light box, as well as on the barrel 130, and can be combined with a carrying strap 120 for use by a technician.

With respect to methods, the gun 100 is powered up, and the emitted beam of UV-C light is directed to a targeted surface having microorganisms to be eradicated. The beam is focused on the targeted surface for time sufficient to eradicate the microorganisms. The method can further include steps of vacuuming away the eradicated microorganisms and by-products by attaching a HEPA vacuum hose to the barrel 130 of the gun 100 in proximity to the nozzle 136. The methods may further include operating an air clarifier in the environment of the remediated surface to clean the air of airborne microorganisms and by-products of the surface remediation.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A high-intensity ultraviolet light gun, the gun comprised of:
   a housing;
   a light box provided within the housing, the light box including a high-intensity UV-C emitting bulb mounted into a bulb housing having electrical terminals for connection to the bulb to complete an electrical circuit, the light box further including a mirror for gathering, reflecting, and directing the high-intensity light emitted from the bulb through a light opening, the light opening communicably connected the first end of an elongated hollow cylindrical tube for receiving, transmitting, and focusing the light into a beam that can be directed to a target;
   a fan for cooling the bulb; and
   a power supply for providing electrical power to an electrical panel provided in the housing, the electrical panel electronically connected to the bulb and the fan.

2. The high-intensity ultraviolet light gun of claim 1, wherein the fan is mounted inside the housing, and wherein the housing includes a vent opening.

3. The high-intensity ultraviolet light gun of claim 1, wherein the fan is mounted on the outside of the housing, and wherein the housing includes a vent opening adjacent the fan.

4. The high-intensity ultraviolet light gun of claim 1, wherein the power supply includes at least one capacitor and at least one transformer to power the gun using electricity provided from a connected external power source.

5. The high-intensity ultraviolet light gun of claim 4, wherein the external power source is selected from the group consisting of 110 volt electrical outlets, 220 volt electrical outlets, rechargeable batteries, and non-rechargeable batteries.

6. The high-intensity ultraviolet light gun of claim 1, wherein the bulb is selected from the group consisting of low pressure-amalgam UV-C bulbs and medium pressure-amalgam UV-C bulbs.

7. The high-intensity ultraviolet light gun of claim 6, wherein the bulb has a wattage rating of between 250 watts and about 1000 watts.

8. The high-intensity ultraviolet light gun of claim 7, wherein the bulb includes a quartz sleeve.

9. The high-intensity ultraviolet light gun of claim 1, wherein the elongated hollow cylindrical tube is comprised of a plurality of interconnecting sections.

10. The high-intensity ultraviolet light gun of claim 9, wherein the interconnecting sections include connecting means.

11. The high-intensity ultraviolet light gun of claim 10, wherein interconnecting means are selected from the group consisting of loops and compatible connecting rods, tabs, slots, threads, and friction fittings.

12. The high-intensity ultraviolet light gun of claim 1, wherein the elongated hollow cylindrical tube includes a reflective internal surface.

13. The high-intensity ultraviolet light gun of claim 12, wherein the polished reflective internal surface is a polished metallic surface.

14. The high-intensity ultraviolet light gun of claim 12, wherein the reflective internal surface is provided as the internal surface of a sleeve inserted into the barrel.

15. The high-intensity ultraviolet light gun of claim 1, wherein the gun further comprises means for automatically powering the bulb for a predetermined time.

16. The high-intensity ultraviolet light gun of claim 15, further comprising means for monitoring the environment of the operating gun and for automatically disabling power to the bulb when motion is detected in the environment.

17. A high-intensity ultraviolet light gun, the gun comprised of:
a housing;
a light box provided within the housing, the light box including a high-intensity UV-C emitting bulb mounted into a bulb housing having electrical terminals for completing an electrical circuit, the light box further including a mirror for gathering, reflecting, and directing the high-intensity light emitted from the bulb through a light opening, the light opening communicably connected the first end of an elongated hollow cylindrical tube for receiving, transmitting, and focusing the light into a beam that can be directed to a target;
a fan for cooling the bulb;
a power supply for providing electrical power to an electrical panel provided in the housing, the electrical panel electronically connected to the bulb and the fan, wherein the power supply includes at least one capacitor and at least one transformer to power the gun using electricity provided from a connected external power source;
wherein the bulb is selected from the group consisting of low pressure-amalgam UV-C bulbs and medium pressure-amalgam UV-C bulbs with a wattage rating of between 250 watts and about 1000 watts, and
wherein the elongated hollow cylindrical tube includes a reflective internal surface.

18. A method of sterilizing a surface, the method comprised of the steps of:
providing a surface having at least one biological contaminant thereon;
operating a portable ultraviolet light gun having a UV-C emitting bulb in communication with a first end of an elongated hollow tube for transmitting emitted ultraviolet light through the tube and out of the opposite end of the tube in a focused and directed beam, a fan for cooling the bulb, and a power supply for providing electrical power to an electrical panel linked to the bulb and the fan;
powering the bulb;
emitting UV-C from the bulb into the first end of the tube;
transmitting the emitted light through the tube and out of the opposite end of the tube in a focused and directed beam; and
directing the focused UV-C to at least one target on the surface for a time sufficient to eradicate at least one biological contaminant on the surface.

19. The method of claim 18, wherein the step of powering the bulb includes powering the bulb for a predetermined time in a manner so as to allow unmanned operation of the gun.

20. The method of claim 19, wherein the method further includes the steps of monitoring the environment of the operating gun and for automatically disabling power to the bulb when motion is detected in the environment.

* * * * *